(12) United States Patent
West et al.

(10) Patent No.: US 11,478,301 B2
(45) Date of Patent: Oct. 25, 2022

(54) MODELING ANATOMICAL STRUCTURES USING AN ANATOMICAL MEASUREMENT WIRE

(71) Applicant: CENTERLINE BIOMEDICAL, INC., Cleveland, OH (US)

(72) Inventors: Karl J. West, Cleveland, OH (US); Vikash R. Goel, Cleveland, OH (US)

(73) Assignee: CENTERLINE BIOMEDICAL, INC., Cleveland, OH (US)

(*) Notice: Subject to any disclaimer, the term of this patent is extended or adjusted under 35 U.S.C. 154(b) by 523 days.

(21) Appl. No.: 16/684,089

(22) Filed: Nov. 14, 2019

(65) Prior Publication Data

US 2020/0155235 A1   May 21, 2020

Related U.S. Application Data

(60) Provisional application No. 62/767,878, filed on Nov. 15, 2018.

(51) Int. Cl.
*A61B 34/10* (2016.01)
*A61B 34/20* (2016.01)
(Continued)

(52) U.S. Cl.
CPC ............. *A61B 34/10* (2016.02); *A61B 5/6847* (2013.01); *A61B 34/20* (2016.02); *G06F 30/20* (2020.01);
(Continued)

(58) Field of Classification Search
CPC ....... A61B 34/10; A61B 5/6847; A61B 34/20; A61B 2034/105; A61B 2034/107;
(Continued)

(56) References Cited

U.S. PATENT DOCUMENTS

2004/0186505 A1* 9/2004 Joergensen ....... A61M 25/0029
604/103.04
2008/0139915 A1    6/2008 Dolan et al.
(Continued)

FOREIGN PATENT DOCUMENTS

| EP | 1504713 A1 | 2/2005 |
| WO | 2013173234 A1 | 11/2013 |
| WO | 2018144969 A1 | 8/2018 |

OTHER PUBLICATIONS

Applicant: Centerline Biomedical, Inc.; International Search Report and Written Opinion; International PCT Application No. PCT/US2019/061493; Filed: Nov. 14, 2019; Authorized Officer: Inho Han; Date of Completion: Mar. 10, 2020; 11pgs.

*Primary Examiner* — Maurice L. McDowell, Jr.
(74) *Attorney, Agent, or Firm* — Tarolli, Sundheim, Covell & Tummnio LLP

(57) ABSTRACT

An example system is disclosed for generating a model of a tubular anatomical structure. The system includes an anatomical measurement wire ("AMW"), a tracking system and a computing device. The AMW is configured to be navigated through the anatomical structure of a patient, and the AMW includes at least one sensor. The tracking system is configured to provide tracking data representing multiple positions of the sensor in a spatial coordinate system. The computing device is configured to generate a data point cloud based on the tracking data, generate a parametric model corresponding to at least a portion of the vessel based on the data point cloud and store the parametric model in non-transitory memory.

20 Claims, 6 Drawing Sheets

(51) Int. Cl.
*A61B 5/00* (2006.01)
*G06F 30/20* (2020.01)
(52) U.S. Cl.
CPC ... *A61B 2034/105* (2016.02); *A61B 2034/107* (2016.02); *A61B 2034/2046* (2016.02)
(58) Field of Classification Search
CPC ...... A61B 2034/2046; A61B 2090/061; A61B 5/02014; A61B 5/062; A61B 5/1076; A61B 5/6851; A61B 90/06; A61B 2017/00867; A61B 2034/2051; A61B 2034/2061; G06F 30/20
See application file for complete search history.

(56) References Cited

U.S. PATENT DOCUMENTS

| | | | |
|---|---|---|---|
| 2011/0160569 A1 | 6/2011 | Cohen et al. | |
| 2014/0276002 A1* | 9/2014 | West | A61B 5/061 600/424 |
| 2015/0164356 A1* | 6/2015 | Merschon | A61B 5/318 600/374 |
| 2016/0015469 A1 | 1/2016 | Kyphon | |
| 2016/0066794 A1 | 3/2016 | Klinder et al. | |
| 2016/0239963 A1 | 8/2016 | Kariv et al. | |
| 2017/0112411 A1* | 4/2017 | Costello | G16H 50/30 |
| 2020/0197106 A1* | 6/2020 | Dekel | A61B 5/065 |

* cited by examiner

MODELING ANATOMICAL STRUCTURES USING AN ANATOMICAL MEASUREMENT WIRE

CROSS-REFERENCE TO RELATED APPLICATION

This application claims the benefit of U.S. Provisional Patent Application 62/767,878 filed on 15 Nov. 2018, and entitled SYSTEMS AND METHODS FOR MODELING AN ANATOMICAL STRUCTURE USING AN ANATOMICAL MEASUREMENT WIRE, the entirety of which is incorporated herein by reference.

TECHNICAL FIELD

This disclosure relates generally to systems and methods for generating a model of an anatomical structure using an anatomical measurement wire.

BACKGROUND

Medical imaging and other medical data associated with an anatomy are commonly available preoperatively and used in a variety of applications such as, for example, in diagnosing medical conditions and in planning and performing medical procedures. Such images and data commonly include a model of anatomy or are commonly used to generate a model of an anatomy. However, current standards of care for certain medical procedures do not include high quality preoperative imaging (e.g., computed tomography or magnetic resonance imaging). For example, the current standard of care for vascular procedures outside the aorta as well as for non-vascular procedures, such as bronchoscopy, typically does not include high quality preoperative imaging.

SUMMARY

In an example, a system is disclosed for generating a model of a tubular anatomical structure. The system includes an anatomical measurement wire ("AMW"), a tracking system and a computing device. The AMW is configured to be navigated through the anatomical structure of a patient, and the AMW includes at least one sensor. The tracking system is configured to provide tracking data representing multiple positions of the sensor in a spatial coordinate system. The computing device is configured to generate a data point cloud based on the tracking data, generate a parametric model corresponding to at least a portion of the vessel based on the data point cloud and store the parametric model in non-transitory memory.

Another example provides a computer-implemented method for generating a model of an anatomical structure. The method includes storing, in one or more non-transitory computer-readable media, tracking data representing a spatial position of sensors operatively coupled to an anatomical measurement wire at a plurality of locations within a lumen the anatomical structure. The method also includes generating a point cloud based on tracking data describing the anatomical measurement wire within the anatomical structure. The method also includes generating a parametric model corresponding to the anatomical structure based on the point cloud. The method also includes storing the parametric model in the non-transitory computer-readable media.

Yet another example provides a computing device configured to execute machine-readable instructions. The instructions are programmed to at least:
generate a data point cloud based on geometry data corresponding to geometry of an anatomical structure of a patient, the geometry data being generated based on tracking at least one sensor fixed to an anatomical measurement wire that is navigated through the anatomical structure of the patient;
generate a parametric model corresponding to the anatomical structure based on the data point cloud; and
generate a visualization of the anatomical structure based on the parametric model.

DETAILED DESCRIPTION

This disclosure relates generally to a system and method for generating a model of an anatomical structure using an anatomical measurement wire ("AMW"). The system and methods described herein can be employed prior to or during a medical procedure, such as an endovascular procedure. The AMW provides a means for collecting geometric information about an anatomical structure of a patient. In examples disclosed herein, the anatomical structure is described as an elongated tubular anatomical construct, such as a blood vessel or other lumen of an organ (e.g., intestine, esophagus, ureter, etc.). The AMW includes one or more sensors from which position and orientation may be determined in a spatial coordinate system. For example, when the AMW is inserted inside a vessel of an anatomy, its position and orientation may be detected to provide geometric information about the vessel according to the location and orientation of each of the (one or more) AMW sensors. For example, a tracking system is configured to track the position and orientation of each AMW sensor as the AWM is moved longitudinally through the anatomical structure. Information collected by the tracking system via the AMW is used to generate a model of an anatomical structure (e.g., a parametric model of the structure). The model can be generated without requiring use of an imaging modality, which enables more widespread use such as at facilities that do not include expensive radiology equipment (e.g., magnetic resonance imaging (MRI), computed tomography (CT) and the similar systems). Moreover, generating a model of an anatomical structure using information collected via the AMW enables use of technology that may rely on and utilize a model of the anatomical structure, such as navigation technology, even in the absence of preoperative imaging. Thus, models of anatomical structures as well as technology which relies on such models may be made available for procedures in which the current standard of care does not include preoperative high quality imaging, such as vascular procedures outside the aorta as well as non-vascular procedures such as bronchoscopy.

Figure 1:
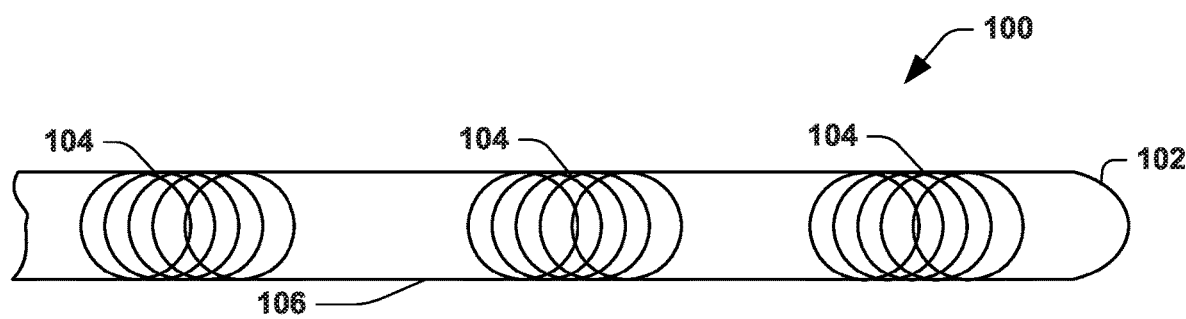
FIG. 1 illustrates an example anatomical measurement wire.

FIG. 1 illustrates an example of an anatomical measurement wire ("AMW") 100. The AMW 100 can be used prior to performing a medical procedure for collecting geometric anatomical information and modeling a patient anatomy. When the model is generated it is inherently registered in a coordinate system of a tracking system used to collect the anatomical information. Accordingly, the model that is generated can facilitate visualizing a medical procedure in which another device (e.g., guidewire or catheter) is inserted into such patient anatomy that has been registered with the model. In one example, the medical procedure can be an endovascular procedure. Such endovascular procedures can include peripheral angioplasty, peripheral stenting, or aortic aneurysm repair, among other procedures.

The AMW 100 is configured to be inserted into a patient (e.g., human or animal) and navigated through one or more anatomical structures of the patient, such as one or more vascular structures (e.g., arteries or veins) or other tubular anatomical structure. The one or more anatomical structures can comprise an elongated tubular vessel structure that includes a lumen. For example, the one or more anatomical structures can include at least one blood vessel, artery, part of a gastrointestinal tract, part of a respiratory tract or part of a reproductive tract. A distal segment 102 of the AMW 100 can be tapered to enable torquability, trackability, pushability and crossability of the AMW 100 through the one or more anatomical structures. In an example, the AMW may include a core wire to improve pushability and/or one or more outer braids to improve torquability of the AMW. The AMW 100 can be biocompatible and have a selected stiffness that is commensurate with an existing guidewire, such as a Glidewire® wire from Terumo Corporation® or a Lunderquirst® wire from Cook Group, Inc.

The AMW 100 can include one or more sensors 104. As an example, the one or more sensors 104 are centrally integrated and embedded at select locations along an elongated body 106 of the AMW 100. For instance, the one or more sensors 104 can be located along an axis (e.g., a central axis or centerline) of the body 106 of the AMW 100. In an example, a plurality of sensors 104 are evenly spaced along the central longitudinal axis of the body of the AMW 100. Additionally, or alternatively, a number of sensors 104 embedded along the axis of the body 106 of the AMW 100 can be set a function of a length of the body 106. It should be appreciated that an increase in the number of sensors 104 strengthens the robustness of the AMW 100. Because the sensors 104 are integrated inside the body 106, the AMW 100 externally resembles an existing conventional guidewire.

In one example, the one or more sensors 104 can respectively spatially sense a plurality of degrees of freedom (DOF). For example, the one or more sensors 104 can be configured to sense five (5) or six (6) DOF, such as corresponding to the Aurora sensor coils available from Northern Digital Inc. In one example, the sensors 104 can be localized using an electromagnetic tracking system (see, e.g., FIG. 5), such as by each sensor generating a tracking signal based on an electromagnetic field that is generated by a field generator of the tracking system. The tracking system 502 thus enables a determination of position and orientation of each sensor 104 based on a sensor signal provided from the sensor to the tracking system in response to an electromagnetic field. Other types of tracking systems (e.g., RFID-type tracking, radiographic tracking, or fiber optic shape sensing) configured to track the position and orientation of each sensor in three-dimensional space may be used.

While inserted in vessel, the AMW 100 provides geometric information about the vessel, namely, geometric information that is based the sensor position and orientation (e.g., provided by the tracking system). For example, the position of each of the sensors 104 provides spatial information about a three-dimensional point geometrically within the vessel. In addition, the orientation of each of the sensors 104 provides an approximation of a tangent vector relative to the vessel's centerline.

The AMW 100 is further configured to be moved (e.g., pulled and/or pushed) axially through the vessel in order to obtain additional information or data points. For example, as the AMW 100 moves through vessel, the position and/or orientation of each of the sensors 104 changes and therefore new information about additional points located within the vessel is provided. For example, the position and/or orientation of each sensor can be tracked by a tracking system at a sample rate as the AMW is moved through the tubular anatomical structure (e.g., a vessel or other structure). Such position and/or orientation for each sensor may be stored in memory to represent the spatial coordinates and orientation of each sensor over a sampling time period. For example, the position and orientation data may be stored as 4×4 homogenous transformation matrices, as quaternions, or as pairs of position vectors and unit direction vectors. Such position and/or orientation information comprise geometry data for the vessel which, for example, is used to generate a parametric model of the anatomical structure, as disclosed herein.

Figure 2A:
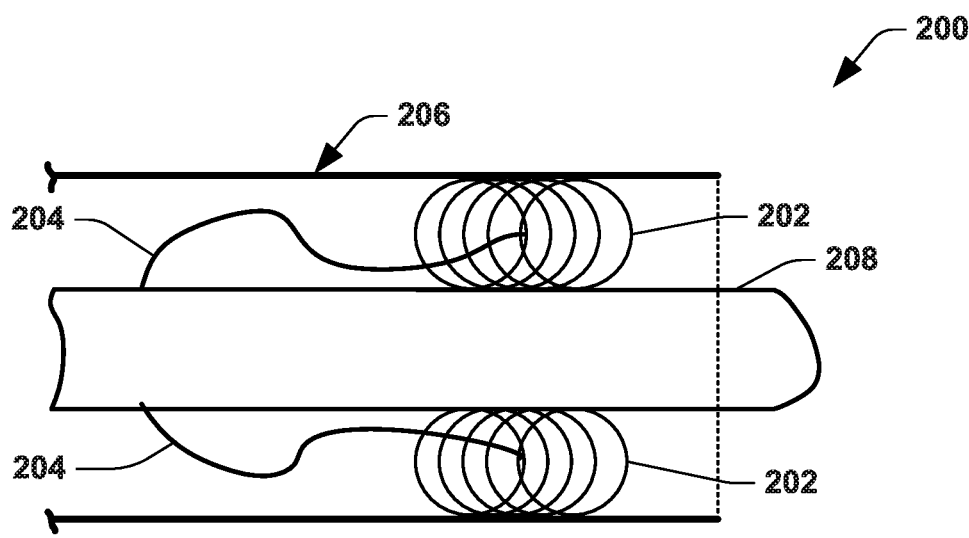
FIGS. 2A and 2B illustrate another example anatomical measurement wire.
Figure 2B:
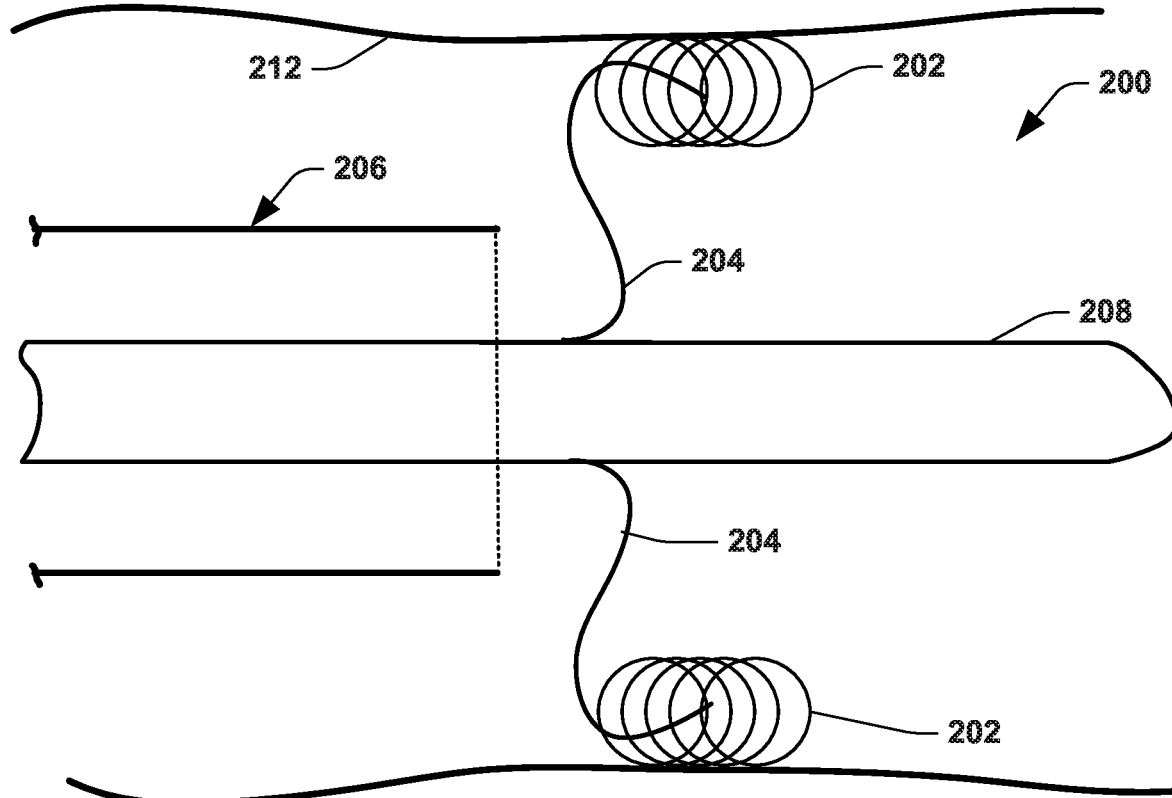

FIGS. 2A and 2B illustrate another example of an anatomical measurement wire ("AMW") 200 that includes one or more tine-mounted electromagnetic sensors 202. In the view of FIGS. 2A and 2B, two tines are shown; although different numbers of tines may be used in other examples. In this example, the sensors 202 are mounted on and/or extend from distal ends of self-expanding tines 204 that are attached to a body 208 of the AMW 200. One end of each tine is fixed to an axial location of the body 208 and the other end of the respective tine is spaced from the body by a length of the tine material. Each tine 204 is mechanically biased to urge its distal end and associated sensor 202 outwardly from the point of attachment on the body 208. Thus, in contrast to sensors 104 being fixed along the body 106 in the example of FIG. 1, the sensors in the example of FIG. 2 are moveable with respect to the body 208 of the AMW 200. As shown in FIG. 2A, the AMW 200 can be packaged inside a catheter 206. Thus, when the catheter sidewall extends along the sensors, the sidewall constrains the tines 204 and the sensors 202 in between the catheter 206 and a body 208 of the AMW 200. The sidewall of the catheter 206 is moveable in an axial direction with respect to the AMW 200. Thus, in response to the catheter sidewall being axially relative to the AMW 200 as to not constrain the sensors (e.g., upon removal of the catheter sidewall from a radially outer extent of the respective sensors), such as shown in FIG. 2B, when placed in a tubular anatomical structure (e.g., a vessel wall) 212, the tines 204 are adapted to urge the distal end thereof and respective sensors 202 radially outwardly from the body 208. The sensors 202 thus can engage the inner sidewall of the lumen. By configuring each of the tines to apply substantially equal force between the inner wall 212 and body 208, a center of the AMW body 208 is positioned at a centroid between the distal ends of the tines, corresponding to a centerline of the anatomical tubular structure (e.g., vessel wall) 212.

As an example, each of the tines 204 is made of material having elastic properties, such as Nitinol (or other shape memory alloy), stainless steel, or another material with elastic properties. The multiple tines 204 can be spaced apart angularly around the AMW body with an evenly distributed angular spacing that depends on the number of tines located at least longitudinal location. For example, the AMW 200 may include two tines at the same longitudinal position along the length of the AMW, and spaced 180 degrees apart from each other circumferentially around the tine body. In another example, where the AMW 200 includes three tines 204, each of the tines is spaced 120 degrees apart from an adjacent tine. Where there are four tines 204, they are spaced 90 degrees apart from each other. By this even distribution of tines at one or more longitudinal location, each of the tines pushes against the interior wall 212 and bias the AMW body to align with the center of the wall structure. The tines may extend from the AMW body a length that may depend on the expected approximate size of the diameter of the vessel being measured. In small vessels for which a priori diameter information is available, the a priori diameter information may be used in lieu of measurement with the tine-mounted sensors.

For example, when the catheter 206 is retracted (e.g., while inside an anatomical structure, such as a vessel, 212), as illustrated in FIG. 2B, the tines 204 self-expand radially outwardly until they press the tines 204 in contact against inner walls of the tubular structure 212. In one example, because the sensors 202 are external to the body 208 and engaging the inner walls of the tubular structure, the AMW 200 may provide additional and improved information about the position of the sidewall 212, as compared to the AMW 100 having sensors 104 centrally integrated along the body 106, as illustrated in FIG. 1. For a multiple tine (e.g., 2 or more tines) example, the tines 204 may extend radially from the AMW body a length that is in a range from under the minimum expected diameter of the vessel to greater than the maximum expected diameter of the vessel, with an oversize intended to ensure the tines are able to reach the inner walls at the maximum and minimum vessel diameters. In this way, the material properties and configuration of the AMW 200 operate to center the body of the AMW within the tubular structure 212 when the tines are free to expand (e.g., not constrained by the catheter 206). The tines may be attached to the body of the AMW 200 such as by welding, with a biocompatible adhesive, or by crimping. The sensors may similarly be attached to the tines by any of these or similar means of attachment.

As a further example, while inserted in vessel, tracking data collected for sensors 202 of the AMW 200 provides geometric information about the vessel. In particular, the three-dimensional position of each of the sensors 202 provides spatial information about a point on the surface of the lumen of the vessel. The center of the tubular structure 212 may be readily determined (e.g., as a centroid) based on the measured spatial position (e.g., three-dimensional coordinates) of the respective sensors at a given axial position of such sensor. In an example, the geometric mean of the position measured by opposing tines at a common axial position along the body 208 (e.g., along a virtual plane extending through the respective sensors and orthogonal to the axis of the tubular structure) provides a position of a point corresponding to an estimate of the centerline of the vessel. Moreover, the mean of the orientation vectors provides a vector proximate to the tangent vector to the vessel's centerline. Thus, the AMW 200 may include one or more sets of tine-mounted sensors 202 to estimate information about the centerline. The average of the orientation vectors of the tine-mounted sensors (e.g., as represented by the tracking data) should yield a vector that is parallel to the centerline of the vessel at the longitudinal position of the tines. As disclosed herein, the geometric information can be used to generate one or more models of the anatomical structure (e.g., a centerline model and/or a surface model), such as a parametric model (e.g., a B-spline or the like).

Figure 3A:
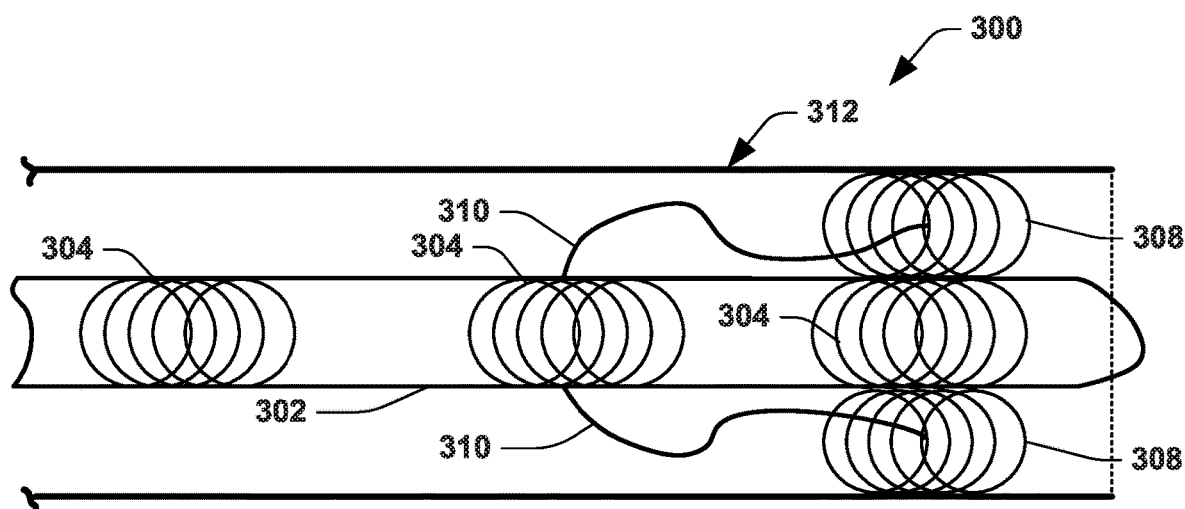
FIGS. 3A and 3B illustrate yet another example anatomical measurement wire.
Figure 3B:
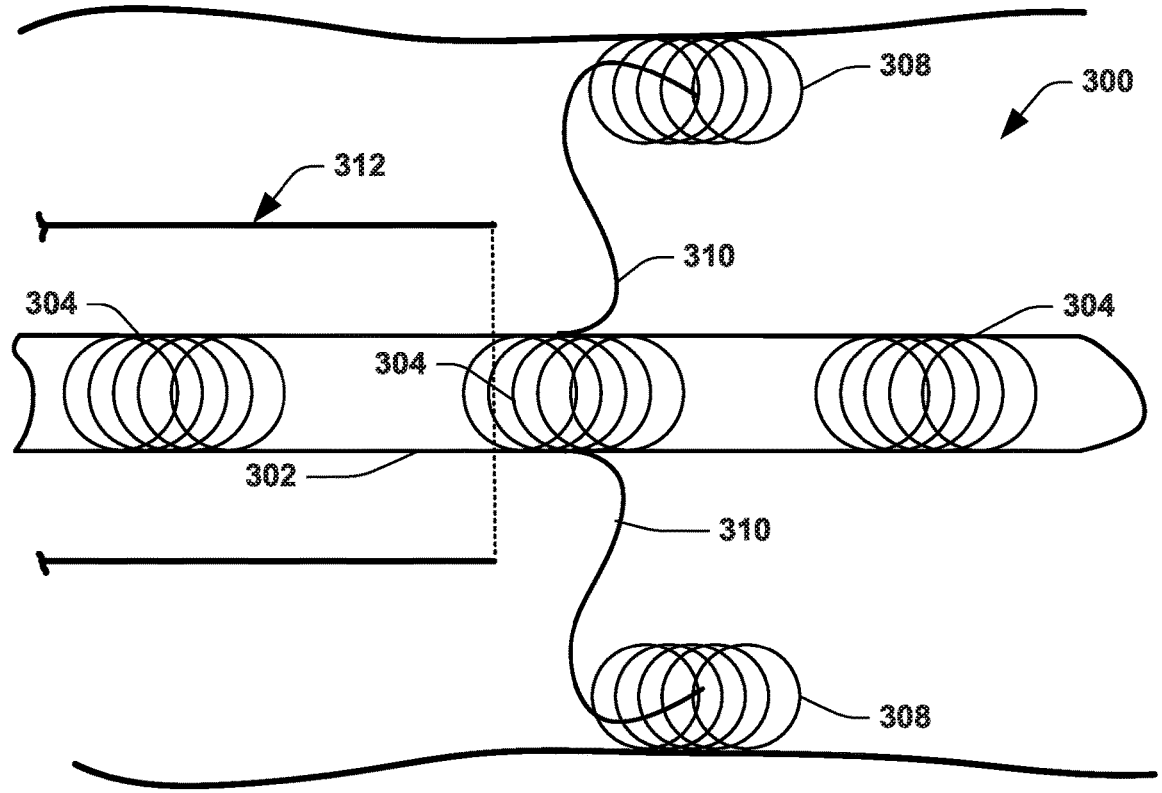

FIGS. 3A and 3B illustrate an example AMW 300 that combines the tines of the AMW 200 of FIG. 2 with the AMW 100 of FIG. 1. Thus, reference may be made to portions of this disclosure for information to such feature. In this example, one or more sets of tines 310 are provided at axial locations along the AMW 300 to help align a central body portion 302 of the AMW along the centerline of the tubular structure during use (when unconstrained—see FIG. 3B). Additionally, use of the AMW according to the method 400 enables geometry data (e.g., position and orientation information) to be collected concurrently for a set of sensors 304 on the body 302 (e.g., located proximal a centerline of the tubular structure 306) and one or more sets of sensors 308 at the end of respective tines 310 engaging the sidewall of the tubular anatomical structure 314.

In the example of FIG. 3A, the AMW 300 is in the constrained condition within a catheter 312, such that the sensors 308 are mechanically biased by respective tines 310 to engage the inner wall of the catheter 312. Thus, the catheter 312 and AMW 300 may be moved collectively as a unit (e.g., within a tubular anatomical structure 314, such as a vessel wall). Once a distal end portion of the unit is at a desired position, the catheter 312 may be pulled axially relative to the AMW 300, either by advancing the body 302 of the AMW beyond the end of the catheter or holding the AMW stationary while the catheter is retracted. Once the sensors 308 are no longer constrained, the tines 310 mechanically bias the sensors 308 radially outwardly from the body 302 and into engagement with the inner wall of tubular anatomical structure 314, such as shown in FIG. 3B. In this position, the sensors 308 are operative to provide position and orientation information along the wall of the structure 314 and the set of sensors 304 on the body 302 of the AMW 300 provide position and orientation information along a centerline within the lumen of the tubular anatomical structure 314. While the examples of FIGS. 2 and 3 show one set of moveable sensors, in other examples, more than one set of two or more moveable sensors each may be implemented on the AMW 300.

Figure 4:
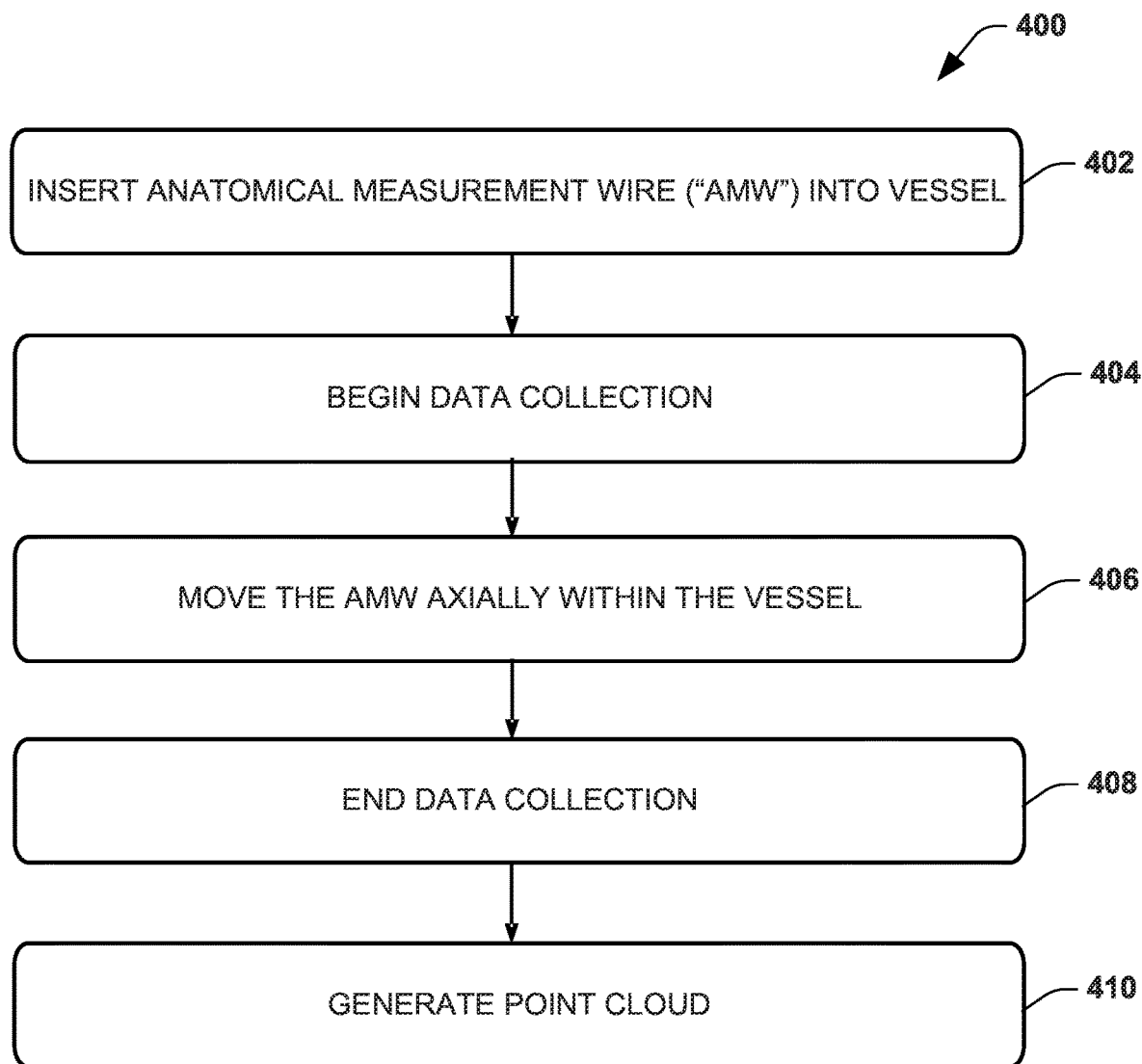
FIG. 4 illustrates an example method for using an example anatomical measurement wire.

The AMW 100 of FIG. 1, the AMW 200 of FIG. 2 and the AMW 300 of FIG. 3 will be further appreciated in the context of describing an example method 400 of using an AMW, as demonstrated in FIG. 4, such as to generate a cloud of data points for an anatomical structure. While, for purposes of simplicity of explanation, the method 400 is shown and described as executing serially, the method 400 is not limited by the illustrated order, as some actions could, in other examples, occur in different orders and/or concurrently with other actions. Moreover, not all illustrated features may be required to implement the method 400 and other features disclosed herein but not shown in FIG. 4 may be used.

At 402, a user inserts the AMW into an anatomical tubular structure (e.g., vessel) of a patient. In an example, the AMW (e.g., AMW 100) is inserted through a vessel, such as to a target location or a target distance through the vessel. In another example, the AMW resides within a catheter (e.g., in a constrained condition, such as shown in FIG. 2A or 3A) to form a unit that is inserted through the vessel for placement of the AMW near the target location. It should be appreciated that the further into the tubular structure (e.g., vessel) that the AMW is inserted, the more data points the AMW will enable collection of. In one example, if accessing the vessel in a retrograde fashion, the AMW is placed as far proximally as feasible. In another example, if accessing the vessel in an antegrade fashion, the AMW is placed as far distally as feasible.

At 404, a data collection process begins. For example, a computer (e.g., computing device 500 of FIG. 5) is configured to execute software or program instructions to control collection of sensor data through communication with a tracking system that receives data from sensors of the AMW and collects data points from the sensors. The sensor data may include three-dimensional position and orientation data collected from the AMW sensors. As disclosed herein, the sensor data for a given sensor (e.g., sensor 104, 202 or 304) provides for an approximate centerline point and/or an approximate surface point when a data point is sampled or collected. The collected data points are stored by the computing device in memory. The sensor data may also be stored in memory of the tracking system.

At 406, the AMW is moved within the vessel, such as may be advanced distally or retracted proximally with respect to a user. The computer executing the program instructions continues to collect data points for each of the sensors of the AMW as the AMW is moved through the vessel. For example, the data points can be acquired by a tracking system (see, e.g., FIG. 5) that is configured to track the position and/or orientation of each sensor in a three-dimensional coordinate system. The process of collecting data points along the length of the structure from the sensors while the AMW is moved through the tubular anatomical structure allows for the collection of many more data points than there are sensors.

Aggregating this collection of data points allows for a formation of a data point cloud which, as disclosed herein can be used to generate an anatomical model of the vessel. As an example, for each frame, the data collected for each sensor is a geometric transformation—a matrix that is adapted to transform from the origin of the tracking system to the origin of the sensor. Different types of tracking systems may report the tracking data in a different but mathematically equivalent form.

As an example, the transformation that forms the tracking data includes a rotation (orientation) and a translation (position) component. A calculation may be performed to separate the rotation and translation components. The translation component for a given sensor within the tubular structure may be represented as spatial coordinates, such as x, y, and z values. The coordinates representing the translation component can then be treated as the coordinates of the origin (typically the center) of the sensor. Thus, each sample from each sensor gives us one three-dimensional geometric point in space. An example of how to compute the x, y, z position from a 4×4 transformation matrix is to use the matrix to transform the homogeneous vector <0, 0, 0, 1>.

In an example, the retraction of the AMW should be performed slowly and steadily in order to improve the accuracy of the collected data points. Moreover, a slower retraction rate may correlate to an increase in number of collected data points. Thus, the retraction rate may be determined or defined by a user based on the amount of data desired to be collected. In one example, a retraction rate may also be determined or defined by a user based on a desired sampling rate. The sampling rate may correspond to a sampling rate of an associated tracking system, for example. The user continues to retract the AMW until the most proximal sensor of the AMW is no longer within the vessel. In one example, feedback via a display or user interface is provided that corresponds to the collected data points in real time as the AMW is being extracted. Thus, a user may adjust the extraction process accordingly based on feedback received via a user interface (e.g., a device or graphical user interface).

As an example, a direct form of feedback would be to plot all of the points in the point cloud in real time, updating them on a 3-D display on the screen as each new sample is added to the point cloud. Thus the user could observe the point cloud being formed. For example, the viewing angle of such 3-D display could be made to automatically change over time to assist in appreciation of the volume of the structure being mapped.

As a further example, an additional feedback mechanism could provide means (e.g., a visualization, an audible indicator or the like) to help the operator retract the device at an appropriate speed. It could take the form of a circle on the screen that is color coded to provide feedback to the user. For example, the circle on the screen may be yellow if the retraction is being done faster or slower than is desired (exceeds a threshold speed), and red if it is too fast to generate a good data (e.g., for at least one sensor in one or more frames of tracking data). Otherwise, the visualization may remain green to indicate that the current speed is within expected parameters for generating a good data. This could, for further example, be accompanied by text appearing on the screen that might state, "Slow down!" when appropriate. For example, a user may slow down or speed up the extraction of the AMW based on received feedback if too many or too few data points are being collected.

At 408, the computer stops collecting data from the sensors. In one example, data collection ends based on user instructions to terminate the method 400. For example, a user may provide input via an interface device (e.g., a mouse, keyboard, button or switch) indicative of when the computer should stop collecting data. At 410, a point cloud is generated by aggregating the collected sensor data, which may include position and orientation data sampled at a plurality of positions along the length of the vessel as the AMW is moved axially at 406. That is, the set of points acquired over time as the AMW is moved through the vessel may be aggregated together to form a cloud of points at 410. For each given sensor that engages the interior wall of the tubular structure, the points lie on the surface of the structure (e.g., vessel wall). For a given sensor that is on the body of the AMW, the points acquired lie on a centerline for the structure (e.g., vessel centerline). The point cloud may be stored in memory as a large array of triplet values, for example. For example, as will be described below, the computing device is configured to generate an anatomical model, corresponding to the vessel, based on the point cloud generated at 410.

Figure 5:
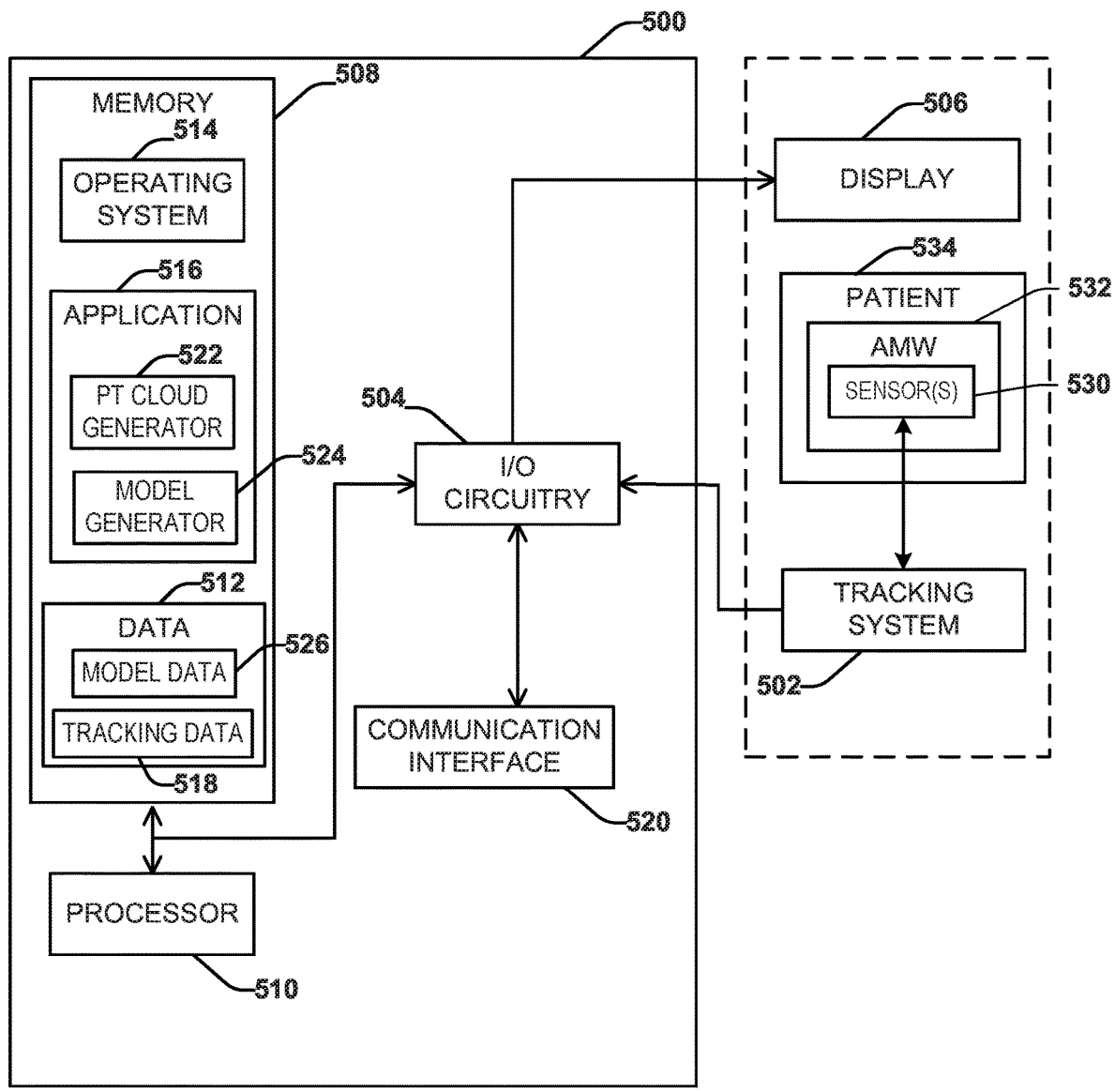
FIG. 5 illustrates an example computer for communicating with sensors of an example anatomical measurement wire and generating an anatomical model.

FIG. 5 illustrates an example of a computing device 500 that can communicate a tracking system 502 via input/output (I/O) circuitry 504. The tracking system 502 is in communication with sensors 530 (e.g., sensors 104, as illustrated in FIG. 1, sensors 202, as illustrated in FIG. 2 and/or sensors 304 and 308, as illustrated in FIG. 3) of an AMW (e.g. AMW 100, as illustrated in FIG. 1, and AMW 200, as illustrated in FIG. 2). The tracking system 502 and configured to provide tracking data representing position and, in some examples, orientation of the sensors 530 as they are navigated through a lumen of an anatomical structure (e.g., vessel) of the patient 534. The tracking system 502 is also configured to aggregate the tracking data to provide tracking sensor data (e.g., position and orientation data) corresponding to geometry of the anatomical structure. The tracking data may be stored in memory of the tracking system 502 and transferred to the computing device through the I/O circuitry and stored in memory 508 (e.g., as tracking data 518). As an example, the tracking system 502 is implemented as an electromagnetic tracking system, such as an electromagnetic sensing system (e.g., one of the Aurora tracking systems from Northern Digital, Inc.). Other types of tracking systems may be used in other examples in conjunction with corresponding sensors 530 for tracking 3D position as the AMW is moved transluminally within the sensing space of the respective tracking system.

For example, if the sensor data is only on the centerline (e.g., using the AMW 100), the registration is only performed using a point cloud (e.g., generated by point cloud generator from tracking data) made up of points along the centerline from the model that is being registered. If the tracking data from the tracking system 502 includes tracking data from sensors only on the walls of the vessels (e.g., from sensors of AMW 200), the centerline is estimated to fall along points directly between opposing tines' measurements (e.g., a mean position from the sensor position data). If the tracking data includes points along both the centerline and walls of the vessel (e.g., from sensors of AMW 300), the point cloud may be generated to include directly measured centerline data and vessel wall data. The processing and aggregation thus may be performed, as disclosed herein, such as to extract the point locations and aggregating such points to construct a large data structure of such points (a data point cloud). The data point cloud can be stored in the memory 508 as tracking data 518.

The computing device 500 can also interface with a display device 506. The display device 506 is communicatively coupled to the computing device 500 (e.g., via the I/O circuitry 504). The computing device 500 can include one or more computing apparatuses that can include memory 508 and one or more processors 510. The memory 508 can be a non-transitory memory that can be configured store machine readable instructions and data 512, such as data collected from the sensors.

By way of example, the memory 508 can store the data 512 and a variety of machine readable instructions, such as including an operating system 514 and, one or more application programs 516. The operating system 514 can be any suitable operating system or combinations of operating systems, which can depend on manufacturer and system to system corresponding to different computer manufacturers. The memory 508 can be implemented, for example as volatile memory (e.g., RAM), nonvolatile memory (e.g., a hard disk, flash memory, a solid state drive or the like) or combination of both. It is to be understood that the memory 508 does not require a single fixed memory but the memory can include one or more non-transitory machine readable memory (e.g., volatile and/or non-volatile memory devices) that can store data and instructions.

The memory 508 can store the data 512 and/or instructions corresponding to the operating system 514 and/or the one or more application programs 516 in a single device or distributed across multiple devices, such as in a network or a cloud computing architecture. In one example, the data 512 includes tracking data 518 characterizing the 3-D position and/or orientation of each of the one or more EM sensors (e.g., sensors 104, 202 or 304 and 308) 530 as collected over time, such as while the AMW 532 is moved axially within the vessel. In this way, the tracking data represents spatial positions along the inner wall of the vessel and/or along the centerline of the vessel.

The processor 510 can access the memory 508 and execute the machine readable instructions to perform respective operations (e.g., corresponding to the operating system 514 and/or the application programs 516). For example, the processor 510 can access the memory 508 to access the one or more application programs 516 which may include a point cloud generator 522 and a model generator 524. The point cloud generator 522, which may be part of or utilized by the model generator 524, is programmed to construct a set of data points in 3-D space (e.g., spatial domain of the tracking system) by aggregating tracking data 518 acquired by the tracking system 502 from sensors of the AMW (e.g., using the AMW 100, 200 or 300 according to the method 400).

The model generator 524 is programmed to generate an anatomical model (e.g., a parametric model) of the vessel based on the point cloud generated from the tracking data 518 (e.g., by point cloud generator 522) corresponding to geometry of the anatomical structure. As disclosed herein, the tracking data 518 may include position and orientation provided by the tracking system 502, such as in the form of a transformation that includes a rotation (orientation) and a translation (position) component. Because the anatomical model is generated from the point cloud derived from tracking data 518 for sensors on the AMW, the model inherently is co-registered in the same spatial domain as the tracking system. Accordingly, other objects (e.g., devices carrying one or more sensors) can be detected by the tracking system and visualized spatially accurately with respect to a graphical representation of the model without requiring further registration.

As an example, the model generator 524 is configured to fit the points of the data point cloud, corresponding the anatomical structure, to a parametric curve that defines a parametric model. For instance, the model generator 524 is configured to estimate the overall length of the curve by measuring the distances between the points of the data point cloud and summing these distances. The model generator 524 is further configured to divide the estimated length into a number of evenly-spaced segments which represent the period between geometric knots of a spline function, such as a B-spline curve. The model generator 524 may further be configured to re-sample the data point cloud at the evenly-spaced segments in order to extract the set of geometric knots. The model generator may employ a B-spline inversion algorithm to compute control points for the B-spline including a parametric centerline model for the tubular anatomical structure (vessel). The resulting anatomical model may be stored in the memory as model data 526.

By way of example, the model data 526 represents a parametric model that has been generated (e.g., by model generator 524) to mathematically represent the geometry of the tubular anatomical structure (the same anatomical structure for which the tracking data 518 is acquired). For example, the parametric model (also referred to as an implicit model) represents a geometric structure by a small number of parameters. Thus, the model data 526 can represent parameters that mathematically define the geometry of a physical anatomical structure of a patient derived from the tracking data acquired by the localizing sensors of the AMW by the tracking system 502. In the example of a tubular anatomical structure (e.g., a vessel), the parametric model includes a set of parameters that define the geometry of a centerline and surface of the tubular anatomical structure.

For example, the model data 526 can include a centerline model representing geometry of the centerline extending axially through the anatomical structure. Additionally or alternatively, the model data 526 can include a surface model describing a surface of the lumen for the anatomical structure that is spaced radially from and circumscribing the centerline. The model parameters for the centerline can be a small set of parameters, such as geometric knots along the centerline, from which control points may be calculated. Additionally, the surface model may be implemented as a lofted b-spline (basis spline) function for the elongated tubular structure.

As a further example, the model data 526 may be an implicit 3-D model of the patient's anatomical structure (e.g., a vessel) of the type disclosed in U.S. Patent Publication No. 2011/0026793 entitled AUTOMATED CENTERLINE EXTRACTION METHOD AND GENERATION OF CORRESPONDING ANALYTICAL EXPRESSION AND USE THEREOF, which is incorporated herein by reference. Another example of generating an implicit model for tubular anatomical structures is disclosed in *Analytical centerline extraction and surface fitting using CT scans for aortic aneurysm repair*, Goel, Vikash R, Master's Thesis, Cornell University (2005), which is incorporated herein by reference. Still another example of generating implicit models for a centerline and surface of tubular anatomical structures is described in the U.S. patent application Ser. No. 16/265,732, which is incorporated herein by reference. Other approaches for generating the implicit model data can also be utilized, such as International Publication No. WO/2014/151651. Various other types of geometric representations can also be utilized to provide the model data 526. For example, parameters representing lofted ellipses or triangular meshes can be generated to provide the anatomical model data 526 representing the patient's anatomical structure of interest.

In an example where the sensors 530 from which the data point cloud is collected are centrally mounted on an anatomical measurement wire ("AMW"), such as the AMW 100 of FIG. 1, the computed parametric centerline comprises actual data points from the data point cloud since the data points represent points sensed at the body of the AMW which is positioned at the center of a vessel. It should be further appreciated that, when the sensors 530 from which the data point cloud is collected are tine-mounted on an AMW, such as the AMW 200 of FIG. 2, the computed parametric centerline comprises points in between the data points from the data point cloud since the data points represent points sensed external to the body of the AWM, along multiple lines of the vessel wall.

The model generator 524 further may be programmed to estimate the diameter of the vessel. In an example where an AMW with centrally mounted sensors along the body of the AMW, such as the AMW 100 or 300, is used to provide the data point cloud, the model generator 524 may estimate the diameter of the vessel based on predefined data such as a patient's height, weight, gender and/or age. Alternatively, when an AMW with tine-mounted sensors, such as the AMW 200 or 300, is used to obtain the data point cloud, the model generator is configured to estimate the diameter of the vessel at each geometric knot by calculating a distance between the points sensed along the multiple lines of the vessel wall. It should be appreciated that, in one example, if diameter information for a vessel is known or can be approximated based on patient information such as height, weight, gender and/or age, the model generator may be configured to utilize the known or approximate diameter information rather than to estimate the diameter, even when an AMW with tine-mounted sensors is used to obtain the data point cloud.

The model generator 524 may further be configured to approximate the cross section of the vessel at each geometric knot as a circle centered on the geometric knot having the estimated diameter, orthogonal to a tangent vector estimated at that point. The model generator may estimate the cross section as a circle because a vessel commonly comprises a generally circular cross section. However, the model generator 524 may similarly be configured to approximate the cross section to have any other suitable shape. The model generator 524 is further configured to loft the circular cross-sections together, thereby providing an approximate parametric model of the surface of the vessel.

The application programs 516 can further include an output generator (not shown) that is configured generate visualization data, which can be provided to the display 506 to render one or more graphical representations. The output generator can generate the visualization data based on the collected and processed data points. As disclosed herein, this may include the acquisition process, including feedback to the user of the AMW during acquisition. Additionally, the output generator can be configured generate a visualization of a graphical representation of the registration process.

Figure 6:
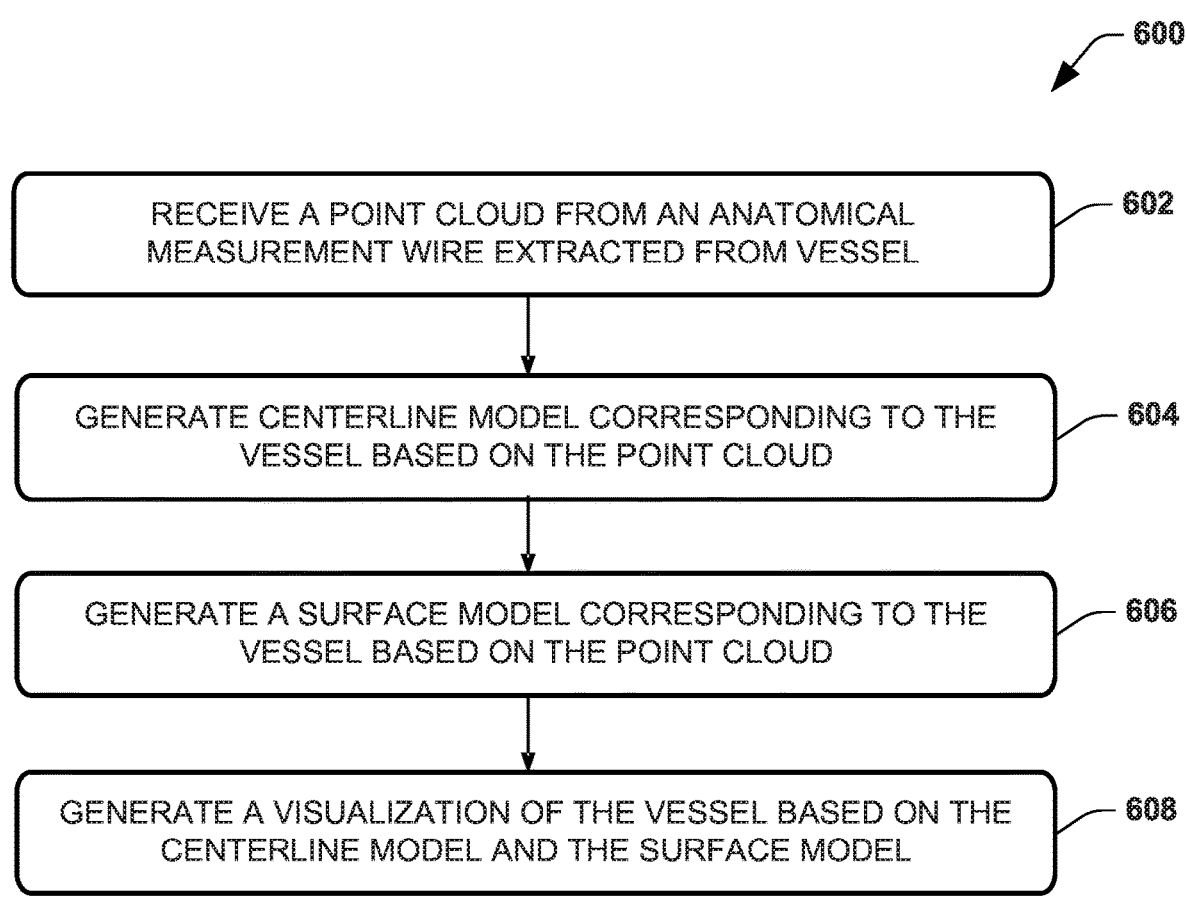
FIG. 6 illustrates an example method for generating a model of based on data acquired from anatomical measurement wire.

In view of the foregoing structural and functional features described above, an example method 600 is demonstrated in FIG. 6. While, for purposes of simplicity of explanation, the method 600 is shown and described as executing serially, the method 600 is not limited by the illustrated order, as some actions could, in other examples, occur in different orders and/or concurrently with other actions. Moreover, not all illustrated features may be required to implement the method 600 and other features disclosed herein but not shown in FIG. 6 may be used.

FIG. 6 depicts an example method 600 for generating a model of an anatomical structure based on a data point cloud obtained using an example anatomical measurement wire ("AMW") (e.g., AMW 100, as illustrated in FIG. 1, and sensors 202, as illustrated in FIG. 2). The method 600 can be implemented, for example, by a computing device (e.g., the computing device 500, as illustrated in FIG. 5). At 602, the computing device receives a data point cloud from an AMW extracted from a vessel.

At 604, the computing device (e.g., model generator code 524) generates a centerline model corresponding to the vessel based on the data point cloud. In one example, the computing device generates the centerline model by fitting points of the data point cloud to a parametric curve. For example, the computing device estimates the overall length of the curve by measuring the distances between the points of the data point cloud, summing these distances, and dividing the estimated length into a number of evenly-spaced segments, which represent a period between geometric knots of a B-spline curve. The computing device then re-samples the data point cloud at the evenly-spaced segments in order to extract a set of geometric knots. In an example, the computing device implements uses a B-spline inversion algorithm to compute control points for the B-spline including the parametric centerline model. Additionally or alternatively, in other examples, different interpolants (other than a B-spline) may be used as a mathematical construct to describe the geometry for each segments of the centerline of the vessel and fit it to the data point cloud.

At 606, the computing device (e.g., model generator) generates a parametric model corresponding to a surface the vessel based on the data point cloud. In one example, the computing device is configured to generate the parametric model of the vessel by estimating the diameter and approximating the cross section of the vessel at each geometric knot as a circle or ellipse centered on the geometric knot having the estimated diameter, orthogonal to a tangent vector estimated at that point. In another example, such as where the AMW used to provide the data point cloud at 602 includes tine-mounted sensors, the distance between diametrically opposed tines can be calculated from respective position information and used to estimate the vessel diameter. In an example where point cloud data is generated from an AMW having only body-mounted sensors, the operator may provide (e.g., via user input to the computing device) an estimated vessel diameter based on which vessel it is and the patient information (e.g., the patient's sex, age, height, weight, and/or prior imaging results). The computing device then lofts the circular cross-sections together, thereby providing an approximate parametric model (e.g., a mathematical function) that represents the surface of the vessel.

The resulting model that is generated may be utilized in various applications. For example, the parametric model may be utilized by software to design an implant to fit the specific anatomy precisely. In another example, the parametric model may be used to plan a trajectory and identify one or more target locations for use during an invasive procedure, such as implemented by a robotic surgical instrument. In yet another example, the model may be utilized to perform computerized diagnosis of conditions of the vessel that is model, such as stenosis or aneurysm.

At 608, the computing device generates a visualization of the vessel based on the centerline model and the vessel model. In one example, the computing device communicates the visualization to a display. For example, the computing device generates the visualization of the parametric model by evaluating the model to calculate 3-D points defining a curve and/or surface that can be rendered graphical on a display device (e.g., display 506). The visualization may also (or alternatively) include feedback such as disclosed herein.

It should be appreciated that, although the example systems and methods described herein may refer to vessels, such as blood vessels specifically, the example systems and methods may similarly be used with any suitable elongated tubular portion of an anatomy, such as a trachea, lymphatic ducts, bile ducts, biliary ducts, urinary tract, or esophagus, for example.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system for generating a model of a tubular anatomical structure, the system comprising: an anatomical measurement wire ("AMW") configured to be navigated through the anatomical structure of a patient, the AMW comprising at least one sensor; a tracking system configured to provide tracking data representing multiple positions of the sensor in a spatial coordinate system; and a computing device configured to: generate a data point cloud based on the tracking data; generate a parametric model corresponding to at least a portion of the anatomical structure based on the data point cloud; and store the parametric model in non-transitory memory.

2. The system of claim 1, wherein the at least one sensor of the AMW includes a plurality of sensors at locations spaced axially apart along an elongate body of the AMW.

3. The system of claim 2, wherein the AMW further comprises a plurality of self-expanding tines extending outwardly from the body of the AMW, the tines configured to, when located within a lumen of the anatomical structure, engage a wall of the lumen and mechanically bias the body of the AMW and the plurality of sensors along the elongate body toward alignment with a centerline of the anatomical structure.

4. The system of claim 3, wherein a respective sensor is attached at a distal end of at least two of the plurality of self-expanding tines located at a common axial position along the elongate body of the AMW.

5. The system of claim 1, further comprising a plurality of self-expanding tines extending outwardly from a body of the AMW to terminate in a distal end thereof, wherein the AMW includes a respective sensor attached at the distal end of at least two of the plurality of self-expanding tines.

6. The system of claim 5, wherein the AMW resides inside a lumen of a catheter and is configured to move axially within the lumen with respect to the catheter, and wherein the catheter is adapted to constrain the plurality of tines and associated sensors between a sidewall of the catheter and the body of the AMW.

7. The system of claim 6, wherein, upon removal of the catheter sidewall from a radially outer extent of the respective sensors, the tines are mechanically biased to expand and urge respective sensors radially outwardly from the body of the AMW.

8. The system of claim 1, wherein the computing device is further configured to generate the parametric model to include a centerline model corresponding to a mathematical function describing a centerline extending axially through the anatomical structure based on the data point cloud and/or a surface model of a wall of the anatomical structure that is spaced radially from and circumscribing the centerline based on the data point cloud.

9. The system of claim 1, further comprising a display device, wherein the computing device is further configured to generate a visualization of the anatomical structure based on the parametric model for display on the display device.

10. The system of claim 1, wherein the computing device is further configured to provide visual feedback based on tracking data acquired during movement of the AMW within the anatomical structure.

11. A computer-implemented method for generating a model of an anatomical structure, the method comprising:
    storing, in one or more non-transitory computer-readable media, tracking data representing a spatial position of sensors operatively coupled to an anatomical measurement wire at a plurality of locations within a lumen the anatomical structure;
    generating a point cloud based on tracking data describing the anatomical measurement wire within the anatomical structure;

generating a parametric model corresponding to the anatomical structure based on the point cloud; and storing the parametric model in the non-transitory computer-readable media.

12. The method of claim 11, wherein the anatomical structure is a vessel.

13. The method of claim 11, wherein generating the parametric model further comprises generating a parametric centerline model corresponding to a spline function describing a centerline of the anatomical structure based on the point cloud.

14. The method of claim 13, wherein generating the parametric model further comprises generating a parametric surface model of a wall of the anatomical structure that is spaced radially from the centerline based on the point cloud.

15. The method of claim 14, further comprising generating a visualization to display a graphical representation of the anatomical structure based on at least one of the parametric centerline model and the parametric surface model.

16. The method of claim 11, wherein the anatomical structure is a tubular anatomical structure, the method further comprising:

moving the anatomical measurement wire through the anatomical structure, the anatomical measurement wire including at least one sensor; and generating tracking data, via a tracking system, corresponding to position and orientation of the at least one sensor as the anatomical measurement wire is moved through the tubular anatomical structure, the point cloud being derived from the tracking data.

17. The method of claim 16, further comprising providing visual feedback based on tracking data acquired during the movement of the AMW within the lumen of the anatomical structure.

18. The method of claim 16, wherein the anatomical measurement wire further comprises a plurality of self-expanding tines extending outwardly from a body of the anatomical measurement wire, and wherein the at least one sensor comprises a plurality of sensors disposed on the body of the anatomical measurement wire and/or at a distal end of respective tines.

19. A computing device configured to execute machine-readable instructions programmed to at least:

generate a data point cloud based on geometry data corresponding to geometry of an anatomical structure of a patient, the geometry data being generated based on tracking at least one sensor fixed to an anatomical measurement wire that is navigated through the anatomical structure of the patient;

generate a parametric model corresponding to the anatomical structure based on the data point cloud; and generate a visualization of the anatomical structure based on the parametric model.

20. The computing device of claim 19, wherein the instructions are further programmed to generate a centerline model corresponding to the anatomical structure based on the data point cloud.

* * * * *